(12) United States Patent
Looker et al.

(10) Patent No.: US 7,321,059 B2
(45) Date of Patent: *Jan. 22, 2008

(54) COMPOUNDS FOR USE AS SURFACTANTS

(75) Inventors: Brian Edgar Looker, Stevenage (GB); Christopher James Lunniss, Stevenage (GB); Alison Judith Redgrave, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 299 days.

This patent is subject to a terminal disclaimer.

(21) Appl. No.: 10/492,606

(22) PCT Filed: Oct. 17, 2002

(86) PCT No.: PCT/EP02/11635

§ 371 (c)(1),
(2), (4) Date: Apr. 15, 2004

(87) PCT Pub. No.: WO03/035237

PCT Pub. Date: May 1, 2003

(65) Prior Publication Data

US 2005/0048024 A1    Mar. 3, 2005

(30) Foreign Application Priority Data

Oct. 19, 2001    (GB) ................. 0125127.1

(51) Int. Cl.
| C07C 59/00 | (2006.01) |
| C07C 59/10 | (2006.01) |
| C07C 69/66 | (2006.01) |
| A61M 11/00 | (2006.01) |

(52) U.S. Cl. .............. 562/587; 562/586; 560/186; 128/200.14

(58) Field of Classification Search ............... 562/512, 562/602, 605, 579, 586, 587, 588, 226, 227, 562/179
See application file for complete search history.

(56) References Cited

U.S. PATENT DOCUMENTS

| 4,352,789 A | 10/1982 | Thiel |
| 5,126,123 A | 6/1992 | Johnson |
| 5,282,987 A * | 2/1994 | Balzer et al. ............... 508/517 |
| 5,376,359 A | 12/1994 | Johnson |
| 6,451,287 B1 | 9/2002 | Desimone et al. |

FOREIGN PATENT DOCUMENTS

| WO | WO9111173 | 8/1991 |
| WO | WO9114422 A | 10/1991 |
| WO | WO9200061 | 1/1992 |
| WO | WO9200062 | 1/1992 |
| WO | WO9609816 | 4/1996 |
| WO | WO 0224623 A | 3/2002 |
| WO | WO03013610 A | 2/2003 |

OTHER PUBLICATIONS

Database CA 'Online! Chemical Abstracts Service, Columbus, Ohio, US; Drexler, H.J., et. al: "Mass spectrometric studies on 2,3-dihydroxypropionic acid ether-esters" retrieved from STN Database accession No. 88:5738 XP002243194 RN 64968-63-4 & Chemistry and Physics of Lipids (1977), 20(1), 71-6.

Database CA 'Online! Chemical Abstracts Service, Columbus, Ohio US; Seher, A., et. al.: "Esters of 2,3-dialkoxypropionic acids and their behavior against pancreatic lipase" retrieved from STN Database accession No. 87:179724 XP002243195 see RN 64713-31-1 & Actes Congr. Mond.—Soc. Int. Etude Corps Gras, 13$^{TH}$ (1976), Volume Symp 2, 17-26. Editor(s): Naudet, M.: Ucciani, E.: Uzzan, A. Publisher: Iterg Paris, FR.

* cited by examiner

*Primary Examiner*—Karl Puttlitz
(74) *Attorney, Agent, or Firm*—Alice P. Bradney

(57) ABSTRACT

Compounds of formula (I):

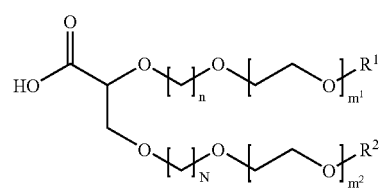

or salts or solvate thereof, wherein:
n and N independently represent an integer 2 to 12;
$m^1$ and $m^2$ independently represent an integer 1 to 15; and
$R^1$ and $R^2$ independently represent —$(CO)_xC_{1-9}$ alkyl or —$(CO)_xC_{1-9}$ fluoroalkyl, which fluoroalkyl moiety contains at least 1 fluorine atom and not more than 3 consecutive perfluorocarbon atoms wherein x represents 0 or 1, as well as pharmaceutical formulations containing such compounds and processes for the manufacture of such compounds are disclosed. Intermediates of such compounds and processes for the manufacture of such intermediates are also disclosed.

42 Claims, No Drawings

COMPOUNDS FOR USE AS SURFACTANTS

This application is filed pursuant to 35 U.S.C. § 371 as a United States National Phase Application of International Patent Application Ser. No. PCT/EP02/11635 filed Oct. 17, 2002, which claims priority from Great Britain Application No. 0125127.1 filed in Great Britain on Oct. 19, 2001.

This invention relates to novel surfactants and aerosol formulations thereof for use in the administration of medicaments by inhalation.

The use of aerosols to administer medicaments has been known for several decades. Such aerosols generally comprise the medicament, one or more chlorofluorocarbon propellants and either a surfactant or a co-solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise fluorocarbons and hydrogen-containing chlorofluorocarbons, and a number of medicinal aerosol formulations using such propellant systems are disclosed in, for example, EP0372777, WO91/04011, WO91/11173, WO91/11495 and WO91/14422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvants such as alcohols, alkanes, dimethyl ether, surfactants (including fluorinated and non-fluorinated surfactants, carboxylic acids, polyethoxylates etc) and even conventional chlorofluorocarbon propellants in small amounts intended to minimise potential ozone damage.

It is essential that the prescribed dose of aerosol medication delivered from the MDI to the patient consistently meets the specifications claimed by the manufacturer and comply with the requirements of the FDA and other regulatory authorities. That is, every dose delivered from the can must be the same within close tolerances. Therefore it is important that the formulation be substantially homogenous throughout the administered dose at the time of actuation of the metering valve. It is also important the dose dispensed does not change substantially after storage.

In the case of suspension formulations, to control aggregation of fine particles and thereby influence the dispersability of the suspension, it is well established in the art that fluorinated surfactants may be used to stabilise micronised drug suspensions in fluorocarbon propellants such as 1,1,1,2-tetrafluoroethane (P134a) or 1,1,1,2,3,3,3-heptafluoro-n-propane (P227), see for example U.S. Pat. No. 4,352,789, U.S. Pat. No. 5,126,123, U.S. Pat. No. 5,376,359, U.S. application Ser. No. 09/580,008, WO91/11173, WO91/14422, WO92/00062 and WO96/09816.

WO92/00061 discloses non-fluorinated surfactants for use with fluorocarbon propellants.

Surprisingly, the applicants have now found that a particular group of novel non-fluorinated and low fluorine content compounds with good surfactant properties may be used to prepare novel aerosol formulations, and may be advantageous in terms of improving the stability of the aerosol formulation, reducing drug deposition, increasing shelf life and the like. In addition the compounds of the invention are adequately soluble in the fluorocarbon or hydrogen-containing chlorofluorocarbon propellants or mixtures thereof, obviating the need to use a polar adjuvant.

Thus, in one aspect the invention provides a compound of the general formula (I)

(I)

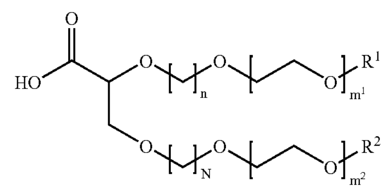

or a salt or solvate thereof, wherein:

n and N independently represent an integer 2 to 12;

$m^1$ and $m^2$ independently represent an integer 2 to 15; and $R^1$ and $R^2$ independently represent $—(CO)_xC_{1-9}$ alkyl or $—(CO)_xC_{1-9}$ fluoroalkyl, which fluoroalkyl moiety contains at least 1 fluorine atom and not more than 3 consecutive perfluorocarbon atoms wherein x represents 0 or 1.

Preferably n and N independently represent an integer 2 to 8, especially 3 to 6.

Preferably $m^1$ and $m^2$ independently represent an integer 2 to 10, especially 3 to 9.

Preferably $R^1$ and $R^2$ independently represent $—(CO)_xC_{1-5}$ alkyl or $—(CO)_xC_{1-5}$ fluoroalkyl, which fluoroalkyl moiety contains at least 1 fluorine atom and not more than 3 consecutive perfluorocarbon atoms. More preferably $—C_{1-3}$alkyl optionally substituted by up to 3 fluorine atoms.

More preferably $R^1$ represents $—C_{1-3}$ alkyl (such as methyl, ethyl, propyl or isopropyl) or $C_{1-3}$ fluoroalkyl$C_{0-6}$ alkylene- (such as $—CHF_2$, $—CF_3$, $—CH_2CF_3$, $—CH_2CF_2CF_3$, $—CF_2CF_3$ or $—(CH_2)_3CF_3CF_3$). Especially preferred is $—CH_3$, $—CF_3$, $—CF_2CF_3$ or $—CH_2CF_3$, especially $—CH_3$ or $—CH_2CF_3$, particularly $—CH_2CF_3$.

More preferably $R^2$ represents $—C_{1-3}$ alkyl (such as methyl, ethyl, propyl or isopropyl) or $C_{1-3}$ fluoroalkyl$C_{0-6}$ alkylene- (such as $—CHF_2$, $—CF_3$, $—CH_2CF_3$, $—CH_2CF_2CF_3$, $—CF_2CF_3$ or $—CH_2)_3CF_3CF_3$). Especially preferred is $—CH_3$, $—CF_3$, $—CF_2CF_3$ or $—CH_2 CF_3$, more especially $—CH_3$ or $—CH_2CF_3$, particularly $—CH_2CF_3$.

Most preferably n will represent the same as N. Most preferably $m^1$ will represent the same as $m^2$. Most preferably $R^1$ will represent the same as $R^2$.

Salts include alkali metal salts such as sodium and potassium and tertiary alkyl ammonium salts such as tert-butyl ammonium.

Preferably compounds of formula (I) will be present as the free acid.

Compounds of formula (I) contain one or more chiral centres. It will be understood that compounds of formula (I) include all optical isomers of the compounds of formula (I) and mixtures thereof, including racemic mixtures thereof.

In a further aspect the invention provides a pharmaceutical aerosol formulation which comprises a particulate medicament, a fluorocarbon or hydrogen-containing chlorofluorocarbon propellant, or mixtures thereof, and a compound of formula (I) as described above.

Surfactant compounds according to the invention may also be useful in solution formulations, for example, to aid the lubrication of the valve and/or assist the solubilisation of the medicament and/or improve the stability of said formulation.

Thus the invention also provides a pharmaceutical formulation which comprises a substantially dissolved medicament and a compound of formula (I) as described above. Preferably the pharmaceutical formulation will be an aerosol formulation which further comprises a fluorocarbon or hydrogen-containing chlorofluorocarbon propellant, or mixtures thereof.

The compounds of formula (I) employed for the preparation of formulations according to the present invention are effective stabilisers at low concentrations relative to the amount of medicament. Thus, the amount of compound of formula (I) employed is desirably in the range of 0.05% to 20% w/w, particularly 0.5% to 10% w/w, more particularly 0.5% to 5% w/w, relative to the medicament.

The particle size of the particulate (e.g. micronised) medicament should be such as to permit inhalation of substantially all of the medicament into the lungs or nasal cavity upon administration of the aerosol formulation and will thus be less than 100 microns, desirably less than 20 microns, and preferably will have a mass median aerodynamic diameter (MMAD) in the range 1-10 microns, e.g. 1-5 microns.

The final aerosol formulation desirably contains 0.005-10% w/w, preferably 0.005-5% w/w, especially 0.01-1.0% w/w, of medicament relative to the total weight of the formulation.

Medicaments which may be administered in aerosol formulations according to the invention include any drug useful in inhalation therapy and which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; anti-allergics, e.g. cromoglycate (e.g. as sodium salt), ketotifen or nedocromil (e.g. as sodium salt); antiinfectives e.g. cephalosporins, penicillins, streptomycin, sulphonamides, tetracyclines and pentamidine; anti-histamines, e.g. methapyrilene; anti-inflammatories, e.g. beclomethasone (e.g. as dipropionate), fluticasone (e.g. as propionate), flunisolide, budesonide, rofleponide, mometasone furoate, ciclesonide, triamcinolone acetonide or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; anti-tussives, e.g. noscapine; bronchodilators, e.g. albuterol (e.g. as free base or as sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol, 4-hydroxy-7-[2-[[2-[[3-(2-phenylethoxy)pro-pyl]sulfonyl]ethyl]amino]ethyl-2(3H)-benzothiazolone; diuretics, e.g. amiloride; anti-cholinergics, e.g. ipratropium (e.g. as bromide), tiotropium, atropine or oxitropium; hormones, e.g. cortisone, hydrocortisone or prednisolone; xanthines, e.g. aminophylline, choline theophyllinate, lysine theophyllinate or theophylline; therapeutic proteins and peptides, e.g. insulin or glucagon. It will be clear to a person skilled in the art that, where appropriate, the medicaments may be used in the form of salts, (e.g. as alkali metal or amine salts or as acid addition salts) or as esters (e.g. lower alkyl esters) or as solvates (e.g. hydrates) to optimise the activity and/or stability of the medicament and/or possibly to minimise the solubility of the medicament in the propellant. It will be further clear to a person skilled in the art that where appropriate, the medicaments may be used in the form of a pure isomer, for example, R-albuterol or RR-formoterol.

Particularly preferred medicaments for administration using aerosol formulations in accordance with the invention include anti-allergics, bronchodilators and anti-inflammatory steroids of use in the treatment of respiratory disorders such as asthma, COPD or rhinitis by inhalation therapy, for example cromoglycate (e.g. as sodium salt), albuterol (e.g. as free base or sulphate), salmeterol (e.g. as xinafoate), formoterol (e.g. as fumarate), terbutaline (e.g. as sulphate), reproterol (e.g. as hydrochloride), a beclomethasone ester (e.g. as diprionate), a fluticasone ester (e.g. as propionate). Salmeterol, especially salmeterol xinafoate, albuterol sulphate, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Thus suitable combinations include bronchodilators (e.g. albuterol or isoprenaline) in combination with an anti-inflammatory steroid (e.g. beclomethasone ester); a bronchodilator in combination with an anti-allergic (e.g. cromoglycate). Exemplary combinations also include: ephedrine and theophylline; fenoterol and ipratropium; isoetharine and phenylephrine; albuterol (e.g. as free base or as sulphate) and beclomethasone ester (e.g. as dipropionate); budesonide and formoterol (e.g. as fumarate) which is of particular interest; and salmeterol (particularly as salmeterol xinafoate) and fluticasone ester (e.g. as propionate) also of particular interest.

The propellants for use in the invention may be any fluorocarbon or hydrogen-containing chlorofluorocarbon or mixtures thereof having a sufficient vapour pressure to render them effective as propellants. Preferably the propellant will be a non-solvent for the medicament. Suitable propellants include, for example, $C_{1-4}$hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds, preferably binary mixtures, with other fluorocarbons or hydrogen-containing chlorofluorocarbons for example $CHClF_2$, $CH_2F_2$ and $CF_3CH_3$. Particularly preferred as propellants are $C_{1-4}$hydrogen-containing fluorocarbons such as 1,1,1,2-tetrafluoroethane ($CF_3CH_2F$) and 1,1,1,2,3,3,3-heptafluoro-n-propane ($CF_3CHFCF_3$) or mixtures thereof. Preferably a single fluorocarbon or hydrogen-containing chlorofluorocarbon such as 1,1,1,2-tetrafluoroethane (HFA 134a) or 1,1,1,2,3,3,3-heptafluoro-n-propane (HFA 227) is employed as the propellant, especially preferred is 1,1,1,2-tetrafluoroethane.

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

If desired the propellant may additionally contain a volatile adjuvant such as a saturated hydrocarbon, for example, propane, n-butane, isobutane, pentane and isopentane or a dialkyl ether, for example, dimethyl ether. In general, up to 50% w/w of the propellant may comprise a volatile hydrocarbon, for example 1 to 30% w/w. However, formulations which are substantially free of volatile adjuvants are preferred. In certain cases, it may be desirable to include appropriate amounts of water, which can be advantageous in modifying the dielectric properties of the propellant.

Polar adjuvants which may, if desired, be incorporated into the formulations according to the present invention include e.g. $C_{2-6}$ aliphatic alcohols and polyols such as ethanol, isopropanol and propylene glycol and mixtures thereof. Preferably if use of a polar adjvant is desirable ethanol will be employed. In general only small quantities (e.g. 0.05 to 3.0% w/w) of polar adjuvants are required and the use of quantities in excess of 5% w/w may disadvantageously in suspension formulations tend to dissolve the medicament. Such formulations preferably contain less than 1% w/w, e.g. about 0.1% w/w of polar adjuvant. Polarity may be determined, for example, by the method described in European Patent Application Publication No. 0327777.

As the compounds of formula (I) are adequately soluble in the fluorocarbon or hydrogen-containing chlorofluorocarbon propellant the need to use a polar adjuvant is obviated. This is advantageous as polar adjuvants especially ethanol are not suitable for use with all patient groups. Formulations containing a compound of formula (I) which avoid use of a polar adjuvant are preferred.

In addition to one or more compounds of the general formula (I), the formulations according to the present invention may optionally contain one or more further ingredients conventionally used in the art of pharmaceutical aerosol formulation. Such optional ingredients include, but are not limited to, taste masking agents, sugars, buffers, antioxidants, water and chemical stabilisers.

A particularly preferred embodiment of the invention provides a pharmaceutical aerosol formulation consisting essentially of one or more particulate medicament(s), one or more fluorocarbon or hydrogen-containing chlorofluorocarbon propellant(s) and one or more compound(s) of formula (I).

A further embodiment of the invention is a sealed container capable of withstanding the pressure required to maintain the propellant as a liquid, such as a metered dose inhaler, containing therein the aerosol formulation as described above.

The term "metered dose inhaler" or MDI means a unit comprising a can, a secured cap covering the can and a formulation metering valve situated in the cap. MDI system includes a suitable channelling device. Suitable channelling devices comprise, for example, a valve actuator and a cylindrical or cone-like passage through which medicament may be delivered from the filled canister via the metering valve to the nose or mouth of a patient e.g. a mouthpiece actuator.

As an aspect of this invention there are also provided processes for the preparation of compounds of formula (I).

A process for preparing a compound of formula (I) is provided which comprises:

(a) oxidation of a compound of formula (II)

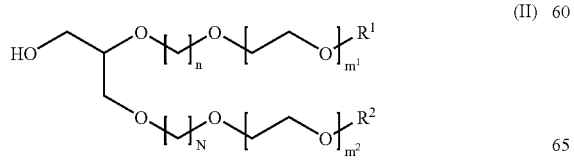

wherein n, N, $m^1$ and $m^2$ are as defined above; or (b) deprotection of a derivative of a compound of formula (I) in which the carboxylic acid group is protected.

In process (a) methods for oxidising a primary alcohol to the corresponding carboxylic acid, using strong oxidising agents, are well known to persons skilled in the art. Suitable reagents include: chromic acid, permanganate (e.g. potassium permanganate) and nitric acid. Permanganate is preferred for use in process (a), especially potassium permanganate.

The oxidation will generally take place in water at non-extreme temperatures, for example, 0 to 60° C. such as room temperature.

In process (b) examples of carboxylic acid protecting groups and means for their removal can be found in "Protecting Groups In Organic Synthesis" by Theodora Green and Peter G. M Wuts (John Wiley and Sons Inc 1999). Suitable carboxylic acid protecting groups include but are not limited to carboxylic acid esters, for example, ethyl ester, aryl esters such as benzyl ester.

Protecting groups can be removed by acid or base catalysed hydrolysis or reduction, for example, hydrogenation. Where the carboxylic acid is protected as the benzyl ester, the protecting group may be removed for example by hydrogenation. Where the carboxylic acid is protected as a $C_{1-3}$ alkyl ester, the protecting group may be removed, for example, by base hydrolysis.

A process for preparing a compound of formula (II) or a protected derivative thereof comprises:

(i) preparing a compound of formula (II), in which $m^2$ represents the same as $m^1$ or a protected derivative thereof, by reacting a compound of formula (III)

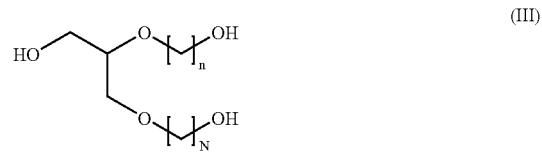

or a protected derivative thereof, wherein n and N are as defined above, with a compound of formula ($IV^1$)

wherein $m^1$ and $R^1$ are as defined above and $L^1$ is a leaving group; or (ii) reacting a compound of formula (V)

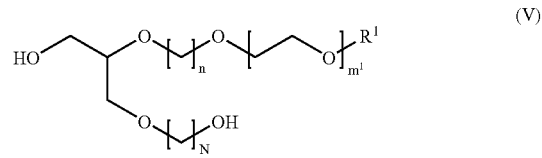

or a protected derivative thereof, wherein n, N, $m^1$ and $R^1$ are as defined above, with a compound of formula (IV²)

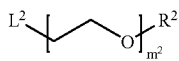
(IV²)

wherein $m^2$ and $R^2$ are as defined above and $L^2$ is a leaving group; or (iii) reacting a compound of formula (VI)

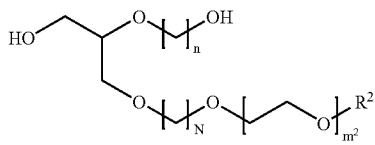
(VI)

or a protected derivative thereof, wherein n, N, $m^2$ and $R^2$ are defined above, with a compound of formula (IV¹) above; or (iv) preparing a compound of formula (II) or a protected derivative thereof, in which $m^2$ represents the same as $m^1$ and N represents the same as n, by reacting a compound of formula (VII)

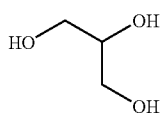
(VII)

or a protected derivative thereof, with a compound of formula (VIII¹)

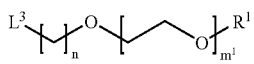
(VIII¹)

wherein n, $m^1$ and $R^1$ are as defined above and $L^3$ is a leaving group; or (v) reacting a compound of formula (IX)

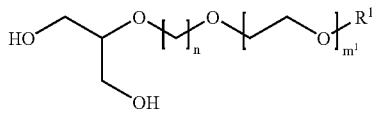
(IX)

or a protected derivative thereof, wherein n, $m^1$ and $R^1$ are as defined above, with a compound of formula (VIII²)

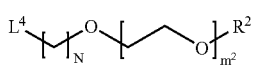
(VIII²)

wherein N, $m^2$ and $R^2$ are as defined above and $L^4$ is a leaving group; or (vi) reacting a compound of formula (X)

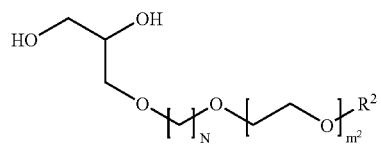
(X)

or a protected derivative thereof, wherein N, $m^2$ and $R^2$ are as defined above, with a compound of formula (VIII¹); or (vii) preparing a compound of formula (II), in which $m^2$ represents the same as $m^1$

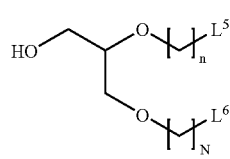
(III¹)

or a protected derivative thereof, by reacting a compound of formula (III¹) or a protected derivative thereof, wherein n and N are as defined above and $L^5$ and $L^6$ represent leaving groups with a compound of formula (XI¹)

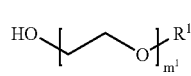
(XI¹)

wherein $m^1$ and $R^1$ are defined above; or (viii) reacting a compound of formula (V¹)

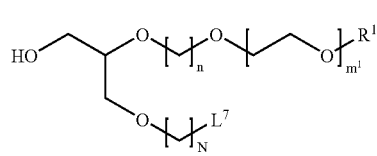
(V¹)

or a protected derivative thereof, wherein n, N, $m^1$ and $R^1$ are defined above and $L^7$ is a leaving group, with a compound of formula (XI²)

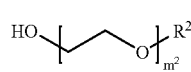
(XI²)

wherein $m^2$ and $R^2$ are as defined above; or (ix) reacting a compound of formula (VI$^1$)

(VI$^1$)

[chemical structure: HO-CH$_2$-CH(O-[CH$_2$]$_n$-L$^8$)-CH$_2$-O-[CH$_2$]$_N$-O-[CH$_2$]$_{m^2}$-OR$^2$]

or a protected derivative thereof, wherein n, N, m$^2$ and R$^2$ are as defined above and L$^8$ is a leaving group, with a compound of formula (XI$^1$) above; or (x) preparing a compound of formula (II) or a protected derivative thereof in (VII$^1$)

[chemical structure: HO-CH$_2$-CH(L$^9$)-CH$_2$-L$^{10}$]

which m$^2$ represents the same as m$^1$ and N represents the same as n by reacting a compound of formula (VII$^1$) or a protected derivative thereof, wherein L$^9$ and L$^{10}$ represent leaving groups with a compound of formula (XII$^1$)

(XII$^1$)

[chemical structure: HO-[CH$_2$]$_n$-O-[CH$_2$]$_{m^1}$-OR$^1$]

wherein n, m$^1$ and R$^1$ are as defined above; or (xi) reacting a compound of formula (IX$^1$)

(IX$^1$)

[chemical structure: HO-CH$_2$-CH(O-[CH$_2$]$_n$-O-[CH$_2$]$_{m^1}$-OR$^1$)-CH$_2$-L$^{11}$]

or a protected derivative thereof, wherein n, m$^1$ and R$^1$ are as defined above and L$^{11}$ is a leaving group, with a compound of formula (XII$^2$)

(XII$^2$)

[chemical structure: HO-[CH$_2$]$_N$-O-[CH$_2$]$_{m^2}$-OR$^2$]

wherein N, m$^2$ and R$^2$ are defined above; or (xii) reacting a compound of formula (X$^1$)

(X$^1$)

[chemical structure: HO-CH$_2$-CH(L$^{12}$)-CH$_2$-O-[CH$_2$]$_N$-O-[CH$_2$]$_{m^2}$-OR$^2$]

or a protected derivative thereof, wherein N, m$^2$ and R$^2$ are as defined above and L$^{12}$ is a leaving group, with a compound of formula (XII$^1$) above; or (xiii) deprotecting a protected compound of formula (II).

In each process the non-reacting hydroxyl group(s) will preferably be protected, for example, as the benzyl or THP ether.

Examples of protecting groups (e.g. for hydroxyl) and means for their removal can be found in "Protecting Groups In Organic Synthesis" by Theodora Green and Peter G. M Wuts (John Wiley and Sons Inc 1999). Suitable hydroxyl protecting groups include, but are not limited to, carboxylic acid esters e.g. acetate ester, aryl esters e.g. benzoate ester, ethers e.g. benzyl ether and p-methoxybenzyl ether, tetrahydropyranyl ether and silyl ethers e.g. tert-butyldimethylsilyl ether. Preferably hydroxyl groups are protected as the benzyl ether or the tetrahydropyranyl (THP) ether. Especially preferred is the benzyl ether.

Protecting groups can be removed by acid or base catalysed hydrolysis or reduction, for example, hydrogenation. Silyl ethers may require hydrogen fluoride or tetrabutylammonium fluoride to be cleaved. Where the hydroxyl is protected as the benzyl ether, the protecting group may be removed, for example, by hydrogenation. Where the hydroxyl is protected as the THP ether, the protecting group may be removed, for example, by acid hydrolysis.

In process (i) suitable leaving groups for L$^1$ include halogen (e.g. chloro, bromide or iodo) —O-tosyl, —O-mesyl or —O-triflyl. Preferably L$^1$ represents —O-tosyl.

The reaction of compounds of formula (III) and (IV$^1$) will generally take place in the presence of a strong base or proton abstracting agent e.g. hydride such as sodium hydride in an inert solvent such as dimethylformamide (DMF) at non-extreme temperatures for example –10 to 50° C. such as 0° C.

Usually at least two molar equivalents of compound of formula (IV$^1$) will be used in this process. Preferably a significant excess of compound of formula (IV$^1$) will be used e.g. 2 to 10 molar equivalents.

In processes (ii), (iii), (iv), (v), (vi), (vii), (viii), (ix), (x), (xi) and (xii) conditions analogous to those employed in process (i) will be suitable. Suitable leaving groups for L$^2$, L$^3$, L$^4$, L$^5$, L$^6$, L$^7$, L$^8$, L$^9$, L$^{10}$, L$^{11}$ and L$^{12}$ include those described above for L$^1$.

Compounds of formula (III) or a protected derivative thereof, wherein N represents the same as n, may be prepared by reacting a compound of formula (XIII$^1$)

$$L^{13}(CH_2)_nOH \quad (XIII^1)$$

or a protected derivative thereof, wherein n is defined as above and L$^{13}$ is a leaving group, examples of which include those above for L$^1$, with a compound of formula (VII), or a protected derivative thereof.

The preparation of compounds of formula (III) from compounds of formula (VII) and (XIII$^1$) will generally take place in the presence of a strong base or proton abstracting agent e.g. hydride such as sodium hydride in an inert solvent e.g. DMF under conditions described above for process (a). At least two molar equivalents of compound of formula (XIII$^1$) will be used. Preferably a significant excess of a compound of formula (XIII$^1$) will be used.

Preferably the non-reacting hydroxyl group(s) will be protected e.g. as the benzyl or THP ether, more preferably by different protecting groups to facilitate selective removal e.g. tetrahydropyranyl (THP) ether and benzyl ether.

Alternatively compounds of formula (III) or a protected derivative thereof may be prepared by reacting compounds of formula (XIV)

(XIV)

[chemical structure: HO-CH$_2$-CH(O-[CH$_2$]$_n$-OH)-CH$_2$-OH]

or a protected derivative thereof, wherein n is as defined above with a compound of formula (XIII$^2$)

$$L^{14}(CH_2)_NOH \quad (XIII^2)$$

or a protected derivative thereof, wherein N is as defined as above and L$^{14}$ is a leaving group, examples of which include those mentioned above for L$^1$.

Conditions analogous to those described above for reaction of compounds of formula (III) and (IV$^1$) may be employed. Preferably the non-reacting hydroxyl groups are protected, more preferably, by different protecting groups to facilitate selective removal e.g. THP ether and benzyl ether.

An alternative process for the preparation of a compounds of formula (III), or a

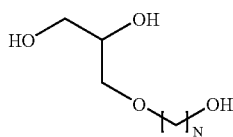
(XV)

protected derivative thereof, comprises reacting a compound of formula (XV) or a protected derivative thereof, with a compound of formula (XIII$^1$) or a protected derivative thereof, employing conditions analogous to those previously described above for the reaction of a compound of formula (III) with a compound of formula (IV$^1$) i.e. in process (i) above. However, variations of these reactions where the leaving group and the reacting hydroxyl are swapped may also be contemplated. Leaving groups will be used as necessary in these reactions.

Compounds of formula (V), or a protected derivative thereof may be prepared by a process which comprises:

(1) reacting a compound of formula (III) or a protected derivative thereof with a compound of formula (IV$^1$), or a protected derivative thereof; or (2) reacting a compound of formula (IX) with a compound of formula (XIII$^1$); or (3) by reacting a compound of formula (IX$^1$) with a compound of formula (XVI$^1$)

HO(CH$_2$)$_n$OH     (XVI$^1$)

or a protected derivative thereof, wherein n is as defined above.

Compounds of formula (VI), (IX), (X), (XIV) and (XV) may be prepared by analogous processes e.g. compounds of formula (VI) can be prepared from compounds of formula (III) and (IV$^2$); compounds of formula (IX) can be prepared from compounds of formula (VII) and (VIII$^1$); compounds of formula (X) can be prepared from compounds of formula (VII) and (VIII$^2$); compounds of formula (XIV) can be prepared from compounds of formula (VII) and (XIII$^1$); compounds of formula (XV) can be prepared from compounds of formula (VII) and (XIII$^2$). In these reactions protecting groups will be employed as necessary.

Compounds of formula (X) can be prepared by a process which comprises:

(1a) reacting epibromohydrin with a compound of formula (XVII)

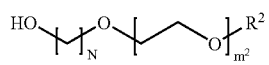
(XVII)

wherein N, m$^2$ and R$^2$ are as defined above under basic conditions; and (2a) reacting the product of step (1a) with water.

Compounds of formula (XV) may be prepared by a process which comprises:

(1b) reacting epibromohydrin with a compound of formula (XVI$^2$)

HO(CH$_2$)$_N$OH     (XVI$^2$)

or a protected derivative thereof, wherein N is as defined above; and (2b) reacting the product of step (1b) with water.

Epoxides can be cleaved under acidic or basic conditions. The product of the reaction can be controlled by choice of the nucleophile. If the ether product is desired the corresponding alcohol or alkoxide should be used as the nucleophile. If the alcohol product is desired water, with an acid catalyst, or hydroxide should be used as the nucleophile.

Compounds of formula (III$^1$) may be prepared from compounds of formula (III), compounds of formula (V$^1$) may be prepared from compounds of formula (V), compounds of formula (VI$^1$) may be prepared from compounds of formula (VI), compounds of formula (VII$^1$) may be prepared from compounds of formula (VII), compounds of formula (IX$^1$) may be prepared from compounds of formula (IX) and compounds of formula (X$^1$) may be prepared from compounds of formula (X) by treatment with a reagent that converts the hydroxyl groups into a leaving group.

Reagents for converting hydroxyl groups into good leaving groups include halogenating agents such as carbon tetrabromide and triphenylphosphine, thionyl chloride or phosphorus pentachloride or by treatment with methane sulphonyl chloride or paratoluene sulphonic chloride. Protecting groups will be used as necessary in these reactions.

Compounds of formula (III$^1$), (V$^1$), (VI$^1$), (VII$^1$), (IX$^1$) and (X$^1$) may also be prepared by methods analogous to those described above for compounds of formula (V), (VI), (IX), (XIV) and (XV) above.

It is also contemplated that compounds of formula (III$^1$), (V), (V$^1$), (VI), (VI$^1$), (VII$^1$), (IX), (IX$^1$), (X), (X$^1$), (XIV) and (XV) may be prepared from epibromohydrin by analogous methods to those described for the preparation of compounds of formula (X) and (XV) above.

The advantage of using epibromohydrin is that the three carbons in the starting material can be differentiated allowing regio-specificity to be introduced with relative efficiency. This is particularly important for compounds of formula (V), (V$^1$), (VI), (VI$^1$), (VII$^1$), (IX), (IX$^1$), (X), (X$^1$), (XIV) and (XV) which are asymmetrical.

Compounds of formula (IV$^1$), (IV$^2$), (VII), (XI$^1$) (XI$^2$), (XII$^1$), (XII$^2$), (XIII$^1$), (XIII$^2$), (XVI$^1$) and (XVI$^2$) are either known or may be prepared by known methods.

Compounds of formula (VIII$^1$), (VIII$^2$) and (XVII) may be prepared by known methods. Variations of the above methods which are common in the art are within the scope of this invention.

Compounds of formula (II), (III), (III$^1$), (VIII$^1$), (VIII$^2$), (V), (V$^1$), (VI), (VI$^1$), (VII$^1$) (IX), (IX$^1$), (X), (X$^1$), (XII$^1$), (XII$^2$), (XIV), (XV) and (XVII) are new and form an aspect of the invention.

In addition processes for preparing formulations including one or more compounds of formula (I) form an aspect of this invention.

The formulations of the invention may be prepared by dispersal of the medicament and a compound of formula (I) in the selected propellant in an appropriate container, e.g. with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The suspension stability of the aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

MDI canisters generally comprise a container capable of withstanding the vapour pressure of the propellant used such as a plastic or plastic-coated glass bottle or preferably a metal can, for example of aluminium or an alloy thereof which may optionally be anodised, lacquer-coated and/or plastic-coated (e.g. incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g., see Byron, above and WO/96/32099). Preferably the canister is fitted with a cap assembly, wherein a formulation metering valve is situated in the cap, and said cap is crimped in place.

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

A further aspect of this invention comprises a process for filling the said formulation into MDIs.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquefied propellant is pressure filled through the charge vessel into a manufacturing vessel, together with liquefied propellant containing the surfactant. The drug suspension is mixed before recirculation to a filling machine and an aliquot of the drug suspension is then filled through the metering valve into the canister.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler system for administration of the medicament into the lungs or nasal cavity of a patient. Metered dose inhalers are designed to deliver a fixed unit dosage of medicament per actuation or "puff", for example in the range of 10 to 5000 micrograms of medicament per puff.

Administration of medicament may be indicated for the treatment of mild, moderate, severe acute or chronic symptoms or for prophylactic treatment. It will be appreciated that the precise dose administered will depend on the age and condition of the patient, the particular particulate medicament used and the frequency of administration will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time.

Suitable daily doses, may be, for example in the range 50 to 200 micrograms of salmeterol, 100 to 1000 micrograms of albuterol, 50 to 2000 micrograms of fluticasone propionate or 100 to 2000 micrograms of beclomethasone dipropionate, depending on the severity of the disease.

Thus, for example, each valve actuation may deliver 25 microgram salmeterol, 100 microgram albuterol, 25, 50, 125 or 250 microgram fluticasone propionate or 50, 100, 200 or 250 microgram beclomethasone dipropionate. Doses for Seretide™, which is a combination of salmeterol and fluticasone propionate, will usually be those given for the corresponding individual component drugs. Typically each filled canister for use in a metered dose inhaler system contains 60, 100, 120, 160 or 240 metered doses or puffs of medicament.

An appropriate dosing regime for other medicaments will be know or readily available to persons skilled in the art.

The use of the compounds of formula (I) as described above especially in the preparation of a pharmaceutical formulation; use of a formulation as described above in inhalation therapy e.g. for the treatment or prophylaxis of respiratory disorders; and use of a metered dose inhaler system in the treatment or prophylaxis of respiratory disorders are all alternative aspects of this invention.

A still further aspect of the present invention comprises a method of treating respiratory disorders such as, for example, asthma or COPD which comprises administration by inhalation of an effective amount of a formulation as herein described.

The following nonlimiting examples serve to illustrate the invention.

EXAMPLES

LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 0% B, 5.3-5.5 min 0% B at a flow rate of 3 ml/min. The mass spectra were recorded on a flow injection Hewlett Packard engine using thermospray positive ion mode or a Micromass series II mass spectrometer using electrospray positive and negative mode (ES+ve and ES−ve).

Example 1

20-(7,10,13,16-Tetraoxaheptadec-1-yloxy)-2,5,8,11, 18-pentaoxahenicosan-21-oic acid (a) 2-({6[2-(Benzyloxy)-1-({[6-(tetrahydro-2H-pyran-2-yloxy)hexyl]oxy}methyl)ethoxy]hexyl}oxy) tetrahydro-2H-pyran To a cooled solution, 0° C., of 1-benzylglycerol (3.00 g) in dimethylformamide (165 ml) was added sodium hydride (60% dispersion in mineral oil, 3.95 g) and the reaction stirred for 45 minutes. 1-Tetrahydropyran-2-yloxy-6-bromohexane (13.10 g) was added and the reaction stirred at 20° C. for 19 hours. The reaction was quenched by the portionwise addition of methanol(10 ml) over 30 minutes at 0° C. The solvent was removed in vacuo and the residue partitioned between water (125 ml) and dichloromethane(125 ml). The organic layer was washed with brine (150 ml), dried and the solvent removed in vacuo. This was purified by column chromatography on silica gel (Biotage) eluting with 8% ethyl acetate in cyclohexane to give the title compound as a pale yellow oil (3.74 g).

$R_f$ 0.34 (8% ethyl acetate in cyclohexane) Mass spectrum m/z 568 $[MNH_4^+]$ (b) 6-(2-(Benzyloxy)-1-{[(6-hydroxyhexyl)oxy] methyl}ethoxy)hexan-1-ol To a stirred solution of the product of step (a) (3.74 g) in methanol (80 ml) was added p-toluenesulphonic acid (260 mg) and the reaction stirred at 20° C. for 24 hours. The solvent was removed in vacuo, the residue dissolved in water (125 ml) and extracted with dichloromethane (3×125 ml). The combined organic layers were washed with brine (150 ml), dried and the solvent removed in vacuo. This was purified by column chromatography on silica gel (Biotage), eluting with 40% ethyl acetate in cyclohexane to give the title compound as a clear oil (1.27 g).

$R_f$ 0.21 (40% ethyl acetate in cyclohexane) Mass spectrum m/z 382.5 $[MH^+]$ (c) 19-[(Benzyloxy)methyl]-2,5,8,11,18,21,28,31,34, 37-decaoxaoctatriacontane The product of step (b) (1.28 g) was dissolved in dimethylformamide (20 ml) and cooled to 0° C. Sodium hydride (60% dispersion in mineral oil, 797 mg) was added slowly and the reaction stirred for 45 minutes. 2-[2-(2-Methoxyethoxy)ethoxy]ethyl 4-methylbenzenesulfonate (3.17 g) was added, and the reaction stirred at 20° C. for 17 hours. The reaction was quenched by the portionwise addition of methanol (10 ml) over 30 minutes at 0° C. The solvent was removed in vacuo, the residue dissolved in water (125 ml) and extracted with dichloromethane (3×125 ml). The combined organic layers were washed with brine (150 ml), dried and the solvent removed in vacuo. Purification by column chromatography on silica gel (Biotage), eluting with 1% methanol in dichloromethane to give the title compound as a clear oil (1.26 g).

$R_f$ 0.36 (1% methanol in dichloromethane) Mass spectrum m/z 692 $[MNH_4^+]$ (d) 20-(7,10,13,16-Tetraoxaheptadec-1-yloxy)-2,5,8, 11,18-pentaoxahenicosan-21-ol A stirred solution of the product of step (c) (1.26 g) and 10% palladium on carbon (126 mg) in 10% acetic acid in ethanol (50 ml) was placed under an atmosphere of hydrogen at 5 atmospheres of pressure for 72 hours. The reaction mixture was filtered through celite, and the solvent removed in vacuo to give the title compound as a clear oil (1.03 g).

$R_f$ 0.26 (3% methanol in DCM) Mass spectrum m/z 585 $[MH^+]$ (e) 20-(7,10,13,16-Tetraoxaheptadec-1-yloxy)-2,5,8, 11,18-pentaoxahenicosan-21-oic acid To a stirred solution of the product of step (d) (207 mg) in an aqueous sodium hydroxide solution (1.98 ml) was added an aqueous potassium permanganate solution (5.58 ml) and the reaction stirred at room temperature for 17 hours. The reaction mixture was filtered, acidified to pH 3 by the addition of hydrochloric acid (2M). This was diluted with water (25 ml) and extracted with DCM (3×25 ml). The combined organic layers were dried and the solvent removed in vacuo to give the title compound as a clear oil.

Retention time 2.92 mins Mass spectrum m/z 597 $[MH^-]$

Other compounds which may be by methods analogous to those given above for Example 1:

Example 2

38-(7,10,13,16,19,22,25,28,31,34-Decaoxapentatriacont-1-yloxy)-2,5,8,11,14,17,20,23, 26,29,36-undecaoxanonatriacontan-39-oic acid Retention time 2.88 mins Mass spectrum m/z 581 $[M/2-NH_4^+]$

Example 3

17-(4,7,10,13-Tetraoxatetradec-1-yloxy)-2,5,8,11,15-pentaoxaoctadecan-18-oic acid Retention time 2.31 mins Mass spectrum m/z 513 $[MH^-]$

Example 4

35-(4,7,10,13,16,19,22,25,28,31-Decaoxadotriacont-1-yloxy)-2,5,8,11,14,17,20,23,26,29,33-undecaoxahexatriacontan-36-oic acid Retention time 2.42 mins Mass spectrum m/z 1040 $[MH^-]$

EXPERIMENTAL DATA

Content Uniformity

Salmeterol xinafoate formulations in HFA 134a, of strength 25 mcg per actuation, and 10% w/w (relative to drug) of the relevant surfactant compound of formula (I) (i.e. Example 3 or Example 4) prepared in aluminum cans with a crimped cap containing a metering valve using salmeterol xinafoate (8.7 mg), HFA 134a (18 g) and the relevant compound (0.87 mg). The control was prepared without the addition of a surfactant. The content uniformity of the formulations was assessed by dose through use testing. Testing was performed on a set of 10 cans/inhalers for each of the formulations, at "beginning of use" (BoU) and "end of use" (EoU). After each inhaler had been primed (4 shots fired to waste), actuations 1 and 2 (BoU) were collected. The next 116 actuations of each inhaler were then fired to waste using an automated method and actuations 119 and 120 (EoU) collected.

The data in Table 1 shows that in the presence of the surfactant compound of Example 3 or Example 4 there was a decrease in the difference between the dose collected at the beginning and end of use. In the control there was a rise from beginning to end of use of 5.6 mcg. However, in the presence of the said surfactant compound this rise was reduced to 1.4 mcg for formulations incorporating a compound of Example 3 and 2.8 mcg for formulations incorporating a compound of Example 4. There was also a reduction in the percentage RSD at BoU for the formulations incorporating said surfactant compounds, thereby showing improved can to can reproducibility. Furthermore, there was also a reduction in the percentage RSD at EoU for the formulations incorporating Example 4. The presence of the said surfactants therefore improves the content uniformity of the inhaler.

TABLE 1

|  | BoU Dose (mcg) | % RSD | EoU Dose (mcg) | % RSD | EoU − BoU (mcg) |
| --- | --- | --- | --- | --- | --- |
| CONTROL | 15.0 | 3.0 | 20.6 | 10.7 | 5.6 |
| Example 3 | 15.8 | 0.7 | 17.2 | 13.9 | 1.4 |
| Example 4 | 16.0 | 1.6 | 18.8 | 5.7 | 2.8 |

Deposition of Drug

Salmeterol xinafoate formulations in HFA 134a, strength 25 mcg per dose for each of 60 actuations, and 10% w/w (relative to drug) of the relevant surfactant compound of formula (I) (i.e. Example 3 or Example 4) were prepared in aluminum cans with a crimped cap containing a metering valve using salmeterol xinafoate (1.50 mg), HFA 134a (3 g) and the relevant compound (0.15 mg). The control was prepared without the addition of a surfactant.

Cans containing the said formulations for analysis were cooled to −4° C. to liquefy the propellant therein. These were then opened and the contents collected in a vessel. The valve and the empty can were quantitatively washed. The washings for each component were kept separate. The amount of drug in: the contents removed from the can, the valve washings and the can washing was quantified by HPLC analysis. The results are presented in Table 2 below.

Table 2 shows that the deposition of drug on the valve and on the can for formulations containing a surfactant compound of Example 3 or Example 4 was lower than the deposition of drug on the canister for the control. Similarly the drug content from cans containing a formulation including one of the said surfactant compounds is significantly higher than for the drug content from the control formulation. Therefore, the presence of said surfactants in formulations seems to reduce the deposition of the drug on the can and valve.

TABLE 2

|  | Valve Deposition (mg) | Can Deposition (mg) | Drug Content In Can (mg) |
| --- | --- | --- | --- |
| CONTROL | 0.46 | 0.55 | 0.31 |
| Example 3 | 0.33 | 0.25 | 0.56 |
| Example 4 | 0.30 | 0.31 | 0.58 |

It will be understood that the present disclosure is for the purpose of illustration only and the invention extends to modifications, variations and improvements thereto which will be within the ordinary skill of the person skilled in the art.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:

1. A compound of formula (I)

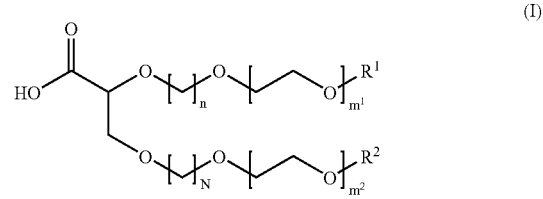

or a salt or solvate thereof wherein:
n and N independently represent an integer 2 to 12;
$m^1$ and $m^2$ independently represent an integer 1 to 15; and
$R^1$ and $R^2$ independently represent $-(CO)_x C_{1-9}$ alkyl, or $-(CO)_x C_{1-9}$ fluoroalkyl, which fluoroalkyl moiety contains at least 1 fluorine atom and not more than 3 consecutive perfluorocarbon atoms
wherein x represents 0 or 1.

2. A compound of formula (I) or a salt or solvate thereof according to claim 1, wherein n and N independently represent an integer 3 to 6.

3. A compound of formula (I) or a salt or solvate thereof according to claim 1, wherein $m^1$ and $m^2$ independently represent an integer 3 to 9.

4. A compound of formula (I) or a salt or solvate thereof according to claim 1, wherein $R^1$ represents $-C_{1-3}$ alkyl or $C_{1-3}$ fluoroalkyl$C_{0-6}$ alkylene-.

5. A compound of formula (I) or a salt or solvate thereof according to claim 4 wherein $R^1$ represents $-CH_3$, $-CH_2CH_3$, $-(CH_2)_2CH_3$, $-CH_2(CH_3)_2$, $-CHF_2$, $-CF_3$, $-CH_2CF_3$, $-CF_2CF_2 CF_3$ or $-CF_2CF_3$.

6. A compound of formula (I) or a salt or solvate thereof according to claim 5 wherein $R^1$ represents $-CF_3$ or $-CH_2CF_3$.

7. A compound of formula (I) or a salt or solvate thereof according to claim 1, wherein $R^2$ represents $-C_{1-3}$ alkyl or $C_{1-3}$ fluoroalkyl$C_{0-6}$ alkylene-.

8. A compound of formula (I) or a salt or solvate thereof according to claim 7, wherein $R^2$ represents $-CH_3$, $-CH_2CH_3$, $-(CH_2)_2CH_3$, $-CH_2(CH_3)_2$, $-CHF_2$, $-CF_3$, $-CH_2CF_3$, $-CF_2CF_2 CF_3$ or $-CF_2CF_3$.

9. A compound of formula (I) or a salt or solvate thereof according to claim 8, wherein $R_2$ represents $-CF_3$ or $CH_2CF_3$.

10. A compound of formula (I) according to claim 1 which is selected from: 20-(7, 10,13,1 6-tetraoxaheptadec-1-yloxy)-2, 5 ,8, 11 , 18-pentaoxabenicosan-2 1-ok acid; 38-(7, 10, 13, 16, 19, 22, 25, 28, 31, 34 -decaoxapentatria-cont -yloxy)-2 ,5 ,8 , 11, 14, 17, 20, 23, 26, 29,3 6-unde-caoxanonatriacontan-39-oic acid; 17-(4, 7, 10, 13-tetraox-atetradec- 1-yloxy) -2, 5, 8, 11, 15-pentaoxaoctadecan-18-oic acid; and 35-(4, 7, 10, 13, 16, 19, 22, 25, 28, 31-decaoxadotriacont-l-yloxy)-2, 5, 8, 11, 14, 17, 20, 23,26, 29,33-undecaoxahexatriacontan-36-oic acid, or a salt or solvate thereof.

11. A compound of formula (I) or a salt or solvate thereof according to claim 2, wherein $m^1$ and $m^2$ independently represent an integer 3 to 9.

12. A compound of formula (I) or a salt or solvate thereof according to claim 2, wherein $R^1$ represents —$C_{1-3}$ alkyl or $C_{1-3}$ fluoroalkyl$C_{0-6}$ alkylene-.

13. A compound of formula (I) or a salt or solvate thereof according to claim 3, wherein $R^1$ represents —$C_{1-3}$ alkyl or $C^{1-3}$ fluoroalkyl$C_{0-6}$ alkylene-.

14. A compound of formula (I) or a salt or solvate thereof according to claim 11, wherein $R^1$ represents —$C_{1-3}$ alkyl or $C_{1-3}$ fluoroalkyl$C_{0-6}$ alkylene-.

15. A compound of formula (I) or a salt or solvate thereof according to claim 12 wherein $R^1$ represents —$CH^3$, —$CH_2CH_3$, —$(C_2)_2CH_3$, —$CH_2(CH_3)_2$, —$CHF_2$, —$CF_3$, —$CH_2CF_3$, —$CH_2CF_2CF_3$ or —$CF_2CF_3$.

16. A compound of formula (I) or a salt or solvate thereof according to claim 13 wherein $R^1$ represents —$CH_3$, —$CH_2CH_3$, —$(CH_2)_2CH_3$, —$CH_2(CH_3)_2$, —$CHF_2$, —$CF_3$, —$C_2CF_3$, —$CH_2CF_2CF_3$ or —$CF_2CF_3$.

17. A compound of formula (I) or a salt or solvate thereof according to claim 14 wherein $R^1$ represents —$CH_3$, —$CH_2CH_3$, —$(CH_2)_2 CH_3$, —$CH_2(CH_3)_2$, —$CHF_2$, —$CF_3$, —$CH_2CF_3$, —$CH_2CF_2CF_3$ or —$CF_2CF_3$.

18. A compound of formula (I) or a salt or solvate thereof according to claim 15 wherein $R_1$ represents —$CF_3$ or —$CH_2CF_3$.

19. A compound of formula (I) or a salt or solvate thereof according to claim 16 wherein $R^1$ represents $CF_3$ or —$CH_2CF_3$.

20. A compound of formula (I) or a salt or solvate thereof according to claim 17 wherein $R^1$ represents —$CF_3$ or —$CH_2CF_3$.

21. A compound of formula (I) or a salt or solvate thereof according to claim 2, wherein $R^2$ represents $C_{1-3}$ alkyl or $C_{1-3}$ fluoroalkyl$C_{0-6}$ alkylene-.

22. A compound of formula (I) or a salt or solvate thereof according to claim 21, wherein $R^2$ represents —$CH_3$, —$CH_2CH_3$, —$(CH_2)_2CH_3$, —$CH_2(CH_3)_2$, —$CHF_2$, —$CF_3$, —$CH_2CF_3$, —$CH_2CF_2CF_3$ or —$CF_2CF_3$.

23. A compound of formula (I) or a salt or solvate thereof according to claim 22, wherein $R^2$ represents $CF_3$ or $CH_2CF_3$.

24. A compound of formula (I) or a salt or solvate thereof according to claim 3, wherein $R^2$ represents —$C_{1-3}$ alkyl or $C_{1-3}$ fluoroalkyl$C_{0-6}$ alkylene-.

25. A compound of formula (I) or a salt or solvate thereof according to claim 24, wherein $R^2$ represents —$CH_3$, —$CH_2CH_3$, —$(CH_2)_2CH_3$, —$CH_2(CH_3)_2$, —$CHF_2$, —$CF_3$, —$CH_2CF_3$, —$CH_2CF_2CF_3$ or —$CF_2CF_3$.

26. A compound of formula (I) or a salt or solvate thereof according to claim 25, wherein $R_2$ represents —$CF_3$ or $CH_2CF_3$.

27. A compound of formula (I) or a salt or solvate thereof according to claim 4, wherein $R^1$ represents —$C_{1-3}$ alkyl or $C_{1-3}$ fluoroalkyl$C_{0-6}$ alkylene-.

28. A compound of formula (I) or a salt or solvate thereof according to claim 27, wherein $R^2$ represents —$CH_3$, —$CH^2CH_3$, —$(CH_2)_2 CH_3$, —$CH_2(CH_3)_2$, —$CHF_2$, —$CF_3$, —$CH_2CF_3$, —$CH_2CF_2CF_3$ or —$CF_2CF_3$.

29. A compound of formula (I) or a salt or solvate thereof according to claim 28, wherein $R_2$ represents —$CF_3$ or $CH_2CF_3$.

30. A compound of formula (I) or a salt or solvate thereof according to claim 5, wherein $R_2$ represents —$C_{1-3}$ alkyl or $C_{1-3}$ fluoroalkyl$C_{0-6}$ alkylene-.

31. A compound of formula (I) or a salt or solvate thereof according to claim 30, wherein $R_2$ represents —$CH_3$, —$CH_2CH_3$, —$(CH_2)_2CH_3$, —$CH_2(CH_3)_2$, —$CHF_2$, —$CF_3$,—$CH_2CF_3$, —$CH_2CF_2CF_3$ or —$CH_2CH_3$.

32. A compound of formula (I) or a salt or solvate thereof according to claim 31, wherein $R_2$ represents —$CF_3$ or $CH_2CF_3$.

33. A compound of formula (I) or a salt or solvate thereof according to claim 6, wherein $R^2$ represents $C_{13}$ alkyl or $C_{1-3}$ fluoroalkyl$C_{0-6}$ alkylene.

34. A compound of formula (I) or a salt or solvate thereof according to claim 33, wherein $R_2$ represents —$CH_3$, —$CH_2CH_3$, —$(CH_2)_2CH_3$, —$CH_2(CH_3)_2$, —$CHF_2$, —$CF_3$, —$CH_2CF_3$, —$CH_2CF_2CF_3$ or —$CF_2CF_3$.

35. A compound of formula (I) or a salt or solvate thereof according to claim 34, wherein $R^2$ represents —$CF_3$ or $CH_2CF_3$.

36. A pharmaceutical aerosol formulation which comprises a particulate medicament, a fluorocarbon or hydrogen-containing chiorofluorocarbon propellant, or mixtures thereof, and a compound of formula (I)

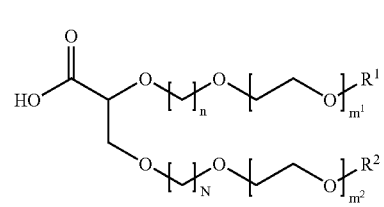

or a salt or solvate thereof, wherein:
n and N independently represent an integer 2 to 12;
$m^1$ and $m^2$ independently represent an integer ito 15; and
$R^1$ and $R^2$ independently represent —$(CO)_xC_{1-3}$ alkyl or —$(CO)_xC_{1-9}$ fluoroalkyl, which fluoroalkyl moiety contains at least 1 fluorine atom and not more than 3 consecutive perfluorocarbon atoms wherein x represents 0 or 1.

37. A pharmaceutical aerosol formulation according to claim 36, wherein the propellant is selected from 1, 1, 1, 2—terrafluoroethane, 1, 1, 1, 2, 3, 3 ,3—heptafluoro-n-propane or mixtures thereof.

38. A pharmaceutical aerosol formulation according to claim 37, containing a combination of two or more particulate medicaments selected from ephedrine and theophylline; fenoterol and ipratropiurn; isoetharine and phenyleplirine; albuterol and beclomerhasone dipropionate, budesonide and formoterol fumarate, salmeterol xinafoate and fluticasone propionate.

39. A sealed container capable of withstanding the pressure required to maintain the propellant as a liquid, said container containing a pharmaceutical aerosol formulation according to claim 36.

40. A metered dose inhaler containing a pharmaceutical aerosol formulation according to claim 36.

41. A metered dose inhaler system containing a pharmaceutical aerosol formulation according to claim 36.

42. A pharmaceutical aerosol formulation which consists essentially of a particulate medicament, a fluorocarbon or hydrogen—containing chlorofuorocarbon propellant, or mixtures thereof, and a compound of formula (I)

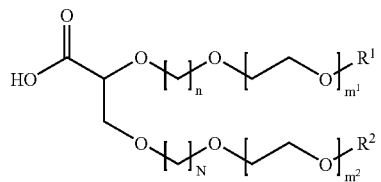

(I)

or a salt or solvate thereof wherein:

n and N independently represent an integer 2 to 12;

$m^1$ and $m_2$ independently represent an integer 1 to 15; and $R^1$ and $R^2$ independently represent —$(CO)_xC_{1-9}$ alkyl or —$(CO)_xC_{1-9}$ fluoroalkyl, which fluoroalkyl moiety contains at least 1 fluorine atom and not more than 3 consecutive perfluorocarbon atoms wherein x represents 0 or 1.

* * * * *

UNITED STATES PATENT AND TRADEMARK OFFICE
CERTIFICATE OF CORRECTION

PATENT NO. : 7,321,059 B2  Page 1 of 3
APPLICATION NO. : 10/492606
DATED : January 22, 2008
INVENTOR(S) : Looker et al.

It is certified that error appears in the above-identified patent and that said Letters Patent is hereby corrected as shown below:

Column 18, Claim 1, line 23 should read:
-- 1. A compound of formula (I) --

Column 18, Claim 5, line 55 should read:
-- -$CH_2CF_3$, -$CH_2CF_2CF_3$ or -$CF_2CF_3$. --

Column 18, Claim 7, line 60 should read:
-- $C_{1-3}$ fluoroalkyl$C_{0-6}$ alkylene-. --

Column 18, Claim 9, line 66 should read:
-- according to claim 8, wherein $R^2$ represents –$CF_3$ or --

Column 19, Claim 10, line 3 should read:
-- 1-yloxy)-2,5,8,11,18-pentaoxabenicosan-21-oic acid; --

Column 19, Claim 10, line 5 should read:
-- cont-1-yloxy)-2,5,8,11,14,17,20,23, 26, 29,36-unde- --

Column 19, Claim 13, line 20 should read:
-- $C_{1-3}$ fluoroalkyl$C_{0-6}$ alkylene-. --

Column 19, Claim 15, line 24 should read:
-- according to claim 12 wherein $R^1$ represents -$CH_3$, --

Column 19, Claim 16, line 30 should read:
-- -$CH_2CF_3$, -$CH_2CF_2CF_3$ or -$CF_2CF_3$. --

Column 19, Claim 18, line 36 should read:
-- according to claim 15 wherein $R^1$ represents –$CF_3$ or --

Column 19, Claim 19, line 39 should read:
-- according to claim 16 wherein $R^1$ represents –$CF_3$ or --

Column 19, Claim 21, line 44 should read:
-- according to claim 2, wherein $R^2$ represents –$C_{1-3}$ alkyl or --

UNITED STATES PATENT AND TRADEMARK OFFICE
CERTIFICATE OF CORRECTION

PATENT NO. : 7,321,059 B2
APPLICATION NO. : 10/492606
DATED : January 22, 2008
INVENTOR(S) : Looker et al.

It is certified that error appears in the above-identified patent and that said Letters Patent is hereby corrected as shown below:

Column 19, Claim 23, line 51 should read:
-- according to claim 22, wherein $R^2$ represents $-CF_3$ or --

Column 19, Claim 26, line 61 should read:
-- according to claim 25, wherein $R^2$ represents $-CF_3$ or --

Column 19, Claim 27, line 64 should read:
-- according to 4, wherein $R^2$ represents $-C_{1-3}$ alkyl or --

Column 20, Claim 29, line 4 should read:
-- according to claim 28, wherein $R^2$ represents $-CF_3$ or --

Column 20, Claim 30, line 7 should read:
-- according to claim 5, wherein $R^2$ represents $-C_{1-3}$ alkyl or --

Column 20, Claim 31, line 10 should read:
-- according to claim 30, wherein $R^2$ represents $-CH_3$, --

Column 20, Claim 31, line 12 should read:
-- $-CF_3$, $-CH_2CF_3$, $-CH_2CF_2CF_3$ or $-CF_2CF_3$. --

Column 20, Claim 32, line 14 should read:
-- according to claim 31, wherein $R^2$ represents $-CF_3$ or --

Column 20, Claim 33, line 16 should read:
-- according to claim 6, wherein $R^2$ represents $-C_{1-3}$ alkyl or $C_{1-3}$ --

Column 20, Claim 34, line 19 should read:
-- according to claim 33, wherein $R^2$ represents $-CH_3$, --

Column 20, Claim 36, line 25 should read:
-- gen-containing chlorofluorocarbon propellant, or mixtures --

Column 20, Claim 36, line 42 should read:
-- $m^1$ and $m^2$ independently represent an integer 1 to 15; and --

UNITED STATES PATENT AND TRADEMARK OFFICE
CERTIFICATE OF CORRECTION

PATENT NO. : 7,321,059 B2
APPLICATION NO. : 10/492606
DATED : January 22, 2008
INVENTOR(S) : Looker et al.

It is certified that error appears in the above-identified patent and that said Letters Patent is hereby corrected as shown below:

Column 20, Claim 36, line 43 should read:
-- $R^1$ and $R^2$ independently represent -(CO)$_x$C$_{1-9}$ alkyl or --

Column 20, Claim 37, line 50 should read:
-- 2-tetrafluoroethane, 1,1,1,2,3,3,3-heptafluoro-n- --

Column 20, Claim 38, line 55 should read:
-- fenoterol and ipratropium; isoetharine and phenylephrine; --

Column 20, Claim 38, line 56 should read:
-- albuterol and beclomethasone dipropionate, budesonide and --

Column 21, Claim 42, line 1 should read:
-- hydrogen-containing chlorofluorocarbon propellant, or --

Column 22, Claim 42, line 3 should read:
-- $m^1$ and $m^2$ independently represent an integer 1 to 15; and --

Signed and Sealed this

Eighth Day of December, 2009

David J. Kappos
*Director of the United States Patent and Trademark Office*